(12) United States Patent
Wilson et al.

(10) Patent No.: US 10,959,873 B2
(45) Date of Patent: Mar. 30, 2021

(54) CUPS FOR COLLECTING CATAMENIA

(71) Applicants: Amanda Wilson, Portland, OR (US);
Steven O'toole Dodson, Gresham, OR (US)

(72) Inventors: Amanda Wilson, Portland, OR (US);
Steven O'toole Dodson, Gresham, OR (US)

(*) Notice: Subject to any disclaimer, the term of this patent is extended or adjusted under 35 U.S.C. 154(b) by 404 days.

(21) Appl. No.: 15/661,384

(22) Filed: Jul. 27, 2017

(65) Prior Publication Data
US 2018/0028350 A1 Feb. 1, 2018

Related U.S. Application Data

(60) Provisional application No. 62/367,322, filed on Jul. 27, 2016.

(51) Int. Cl.
*A61F 5/455* (2006.01)
(52) U.S. Cl.
CPC .................................. *A61F 5/4553* (2013.01)
(58) Field of Classification Search
CPC ................. A61F 5/4553; A61F 5/4556; A61B 2010/0074
See application file for complete search history.

(56) References Cited

U.S. PATENT DOCUMENTS

| | | | | | |
|---|---|---|---|---|---|
| 2,089,113 | A | * | 8/1937 | Chalmers | A61F 5/4553 604/330 |
| 3,626,942 | A | * | 12/1971 | Waldron | A61F 5/4553 604/330 |
| 3,845,766 | A | * | 11/1974 | Zoller | A61F 5/4553 604/330 |
| 2008/0077097 | A1 | * | 3/2008 | Chambers | A61F 5/4553 604/330 |
| 2018/0214298 | A1 | * | 8/2018 | Medas | A61F 5/4553 |

FOREIGN PATENT DOCUMENTS

| FR | 3039060 A1 * | 1/2017 | ........... A61F 5/4553 |
|---|---|---|---|
| WO | WO-2007082341 A1 * | 7/2007 | ........... A61F 5/4553 |

* cited by examiner

*Primary Examiner* — Tatyana Zalukaeva
*Assistant Examiner* — Heather K Barnwell

(57) ABSTRACT

Reusable cups for collecting catamenia having a base, outer and inner walls, apertures, ribs, and ridges. In some examples, the reusable cups include a trimmable stem. In some further examples, the reusable cups include a circumferential band as a double seal for leak protection and to aid the reusable cups in fully expanding upon insertion and while in situ. In further examples, the reusable cups include indentations and indicia at the base of the reusable cups to work in tandem with the ribs and the apertures such that when the reusable cup is pinched at the base, the suction seal at the aperture and the lip is broken.

18 Claims, 7 Drawing Sheets

CUPS FOR COLLECTING CATAMENIA

This application claims priority to U.S. Application, entitled MENSTRUAL CUP, Ser. No. 62/367,322 filed on 27 Jul. 2016, which is hereby incorporated by reference for all purposes.

SUMMARY

The present disclosure is directed to a reusable cup for collecting catamenia having a base, outer and inner walls, apertures, ribs, and ridges. In some examples, the reusable cup includes a trimmable stem. In some further examples, the reusable cup includes a circumferential band.

BACKGROUND

The present disclosure relates generally to feminine hygiene products. In particular, reusable menstrual cups for collecting and disposing of catamenia are described.

Known menstrual cups are not entirely satisfactory for the range of applications in which they are employed. For example, existing menstrual cups can be difficult to use, are uncomfortable, and prone to leaking. They are also difficult to properly clean and sterilize and tend to become dislodged during exercise or other movement. Other cups can be painful to remove because they provide improper suction that does not break at the top of the cup where the seal is formed.

Thus, there exists a need for cups for collecting catamenia that improve upon and advance the design of known menstrual cups. Examples of new and useful menstrual cups relevant to the needs existing in the field are discussed below. The present invention includes features that improve leak protection, placement and retention, removal efficiency, storage, portability, and comfort.

DETAILED DESCRIPTION

The disclosed reusable cups for collecting catamenia will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, a variety of reusable cup examples are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Figure 1:
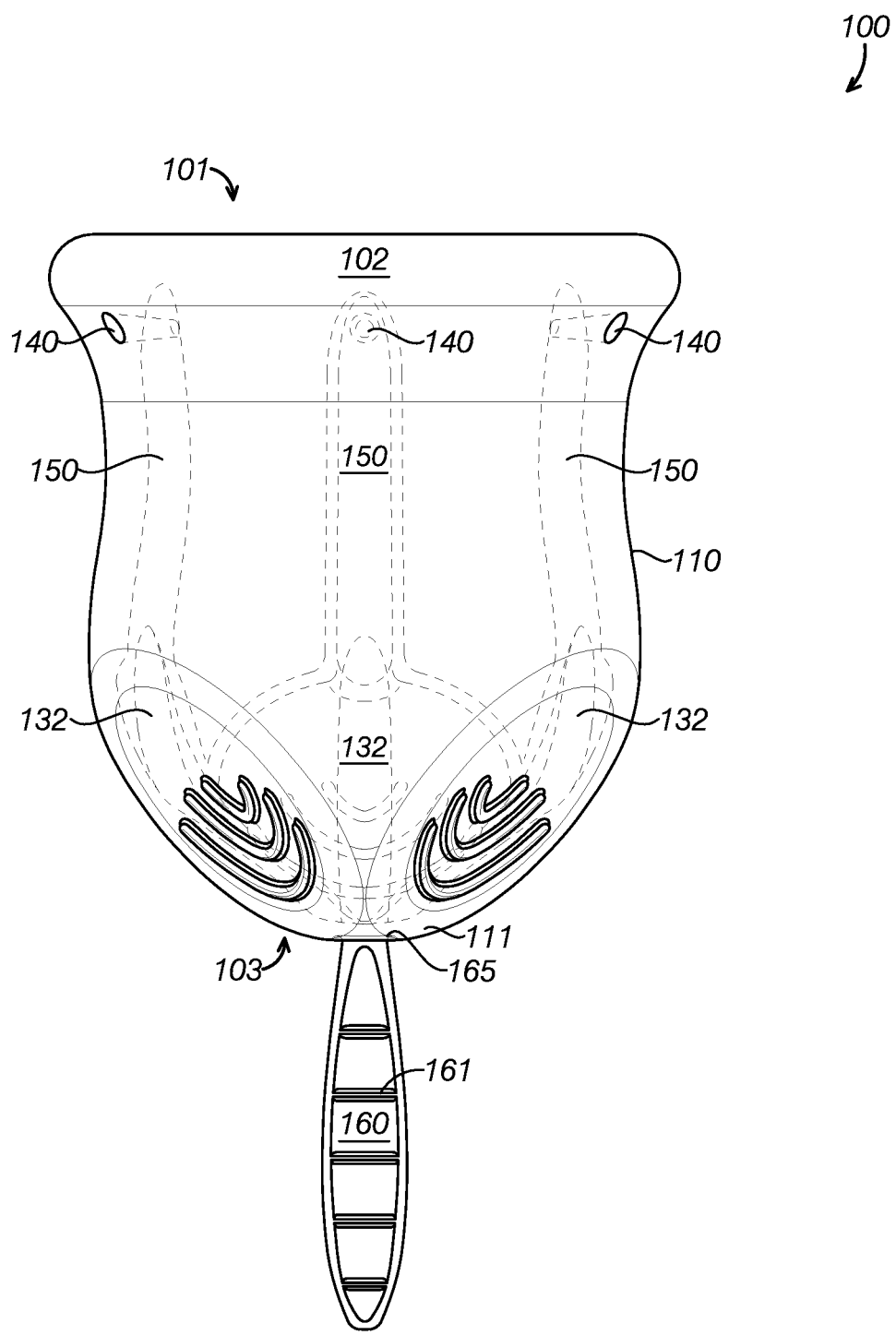
FIG. 1 is perspective view of a first example of a menstrual cup.

With reference to FIG. 1, a first example of a reusable cup for collecting catamenia, cup 100, will now be described. Cup 100 is a menstrual cup that functions to collect catamenia during a woman's menstrual cycle. Cup 100 addresses many of the shortcomings existing with conventional menstrual cups. For example, it comprises a double seal for leak protection, ridges and ribs that aid and hold the expansion of the cup in situ, and a unique ergonomic grip and pinch feature at the base that allows it to be removed and in an efficient and comfortable way. It also includes a unique receptacle that houses a trimmable stem. Further, its overall shape aids in the securement of the cup while the user is active. The present invention further comprises collapsibility for easy insertion, removal, and storage and is designed specifically to minimize movement and irritable rubbing within the body of the user. Finally, in alternative embodiments (not shown) cup 100 may include a uniquely designed storage case for effective storage between uses.

Thus, from the following figures and their descriptions, the reader will appreciate that the present invention is an improved receptacle for collecting catamenia. The reader will appreciate that cup 100 substantially comprises a comfortable, durable, reusable, leak-proof receptacle in which catamenia is collected and transported to an appropriate waste receptacle. In order to use cup 100, the user will collapse cup 100 on the vertical plane and insert it into the vagina. Cup 100 will naturally expand and conform to the user's unique shape and stay in place via gentle suction between the vaginal wall and the outside of cup 100. When the user wishes to remove cup 100, she will collapse cup 100 and break the gentle suction between cup 100 and the vaginal wall and pull cup 100 downward and out of the vagina. She may then empty the contents, sterilize cup 100, and store it in a uniquely configured antimicrobial storage case where it will remain safe and sterile until its next use.

Figure 3:
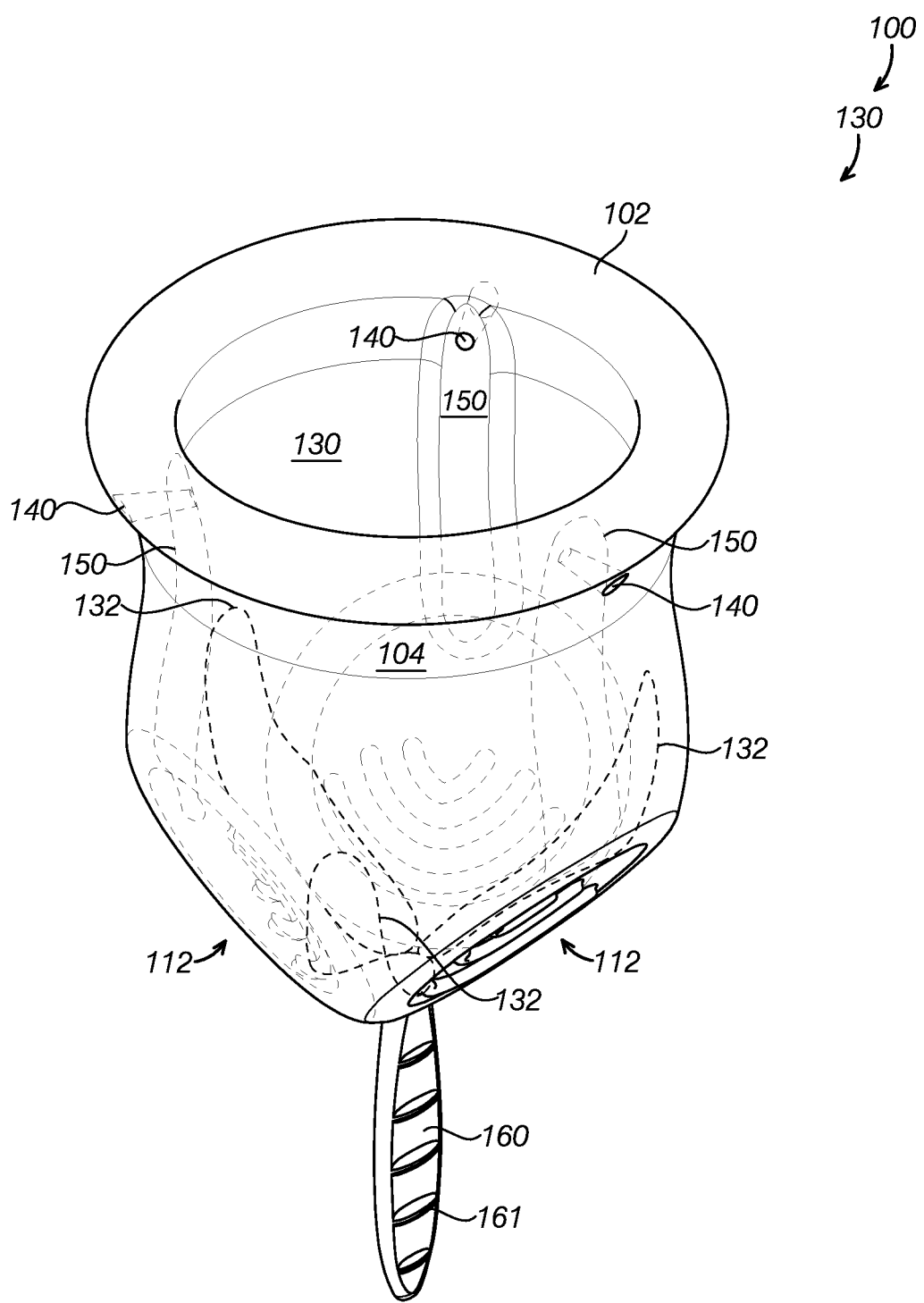
FIG. 3 is a perspective view of the menstrual cup in FIG. 1 depicting the inner wall of the cup.
Figure 4:
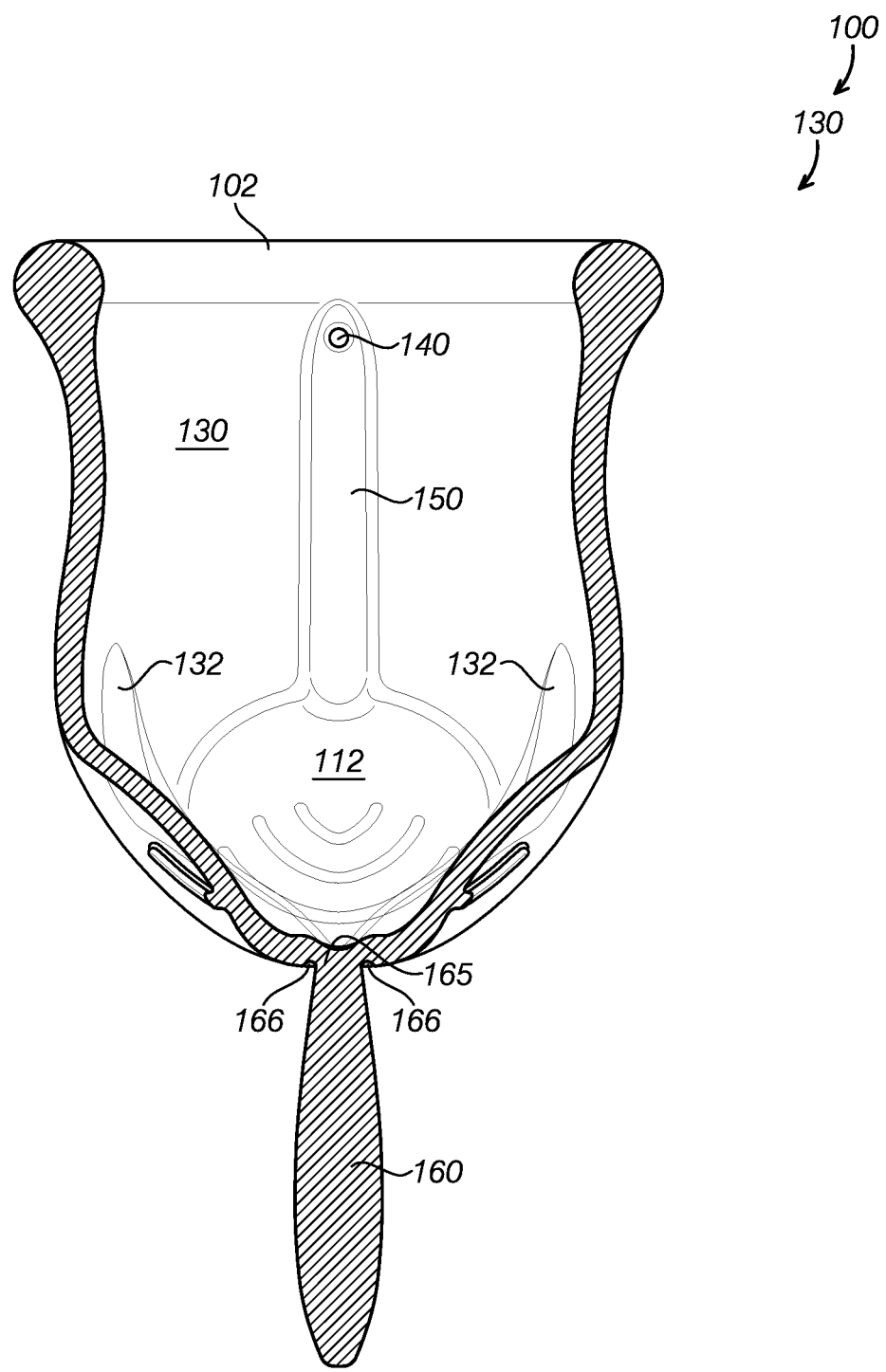
FIG. 4 is a bisected view of the menstrual cup in FIG. 1 depicting the inner wall of the cup.
Figure 5:
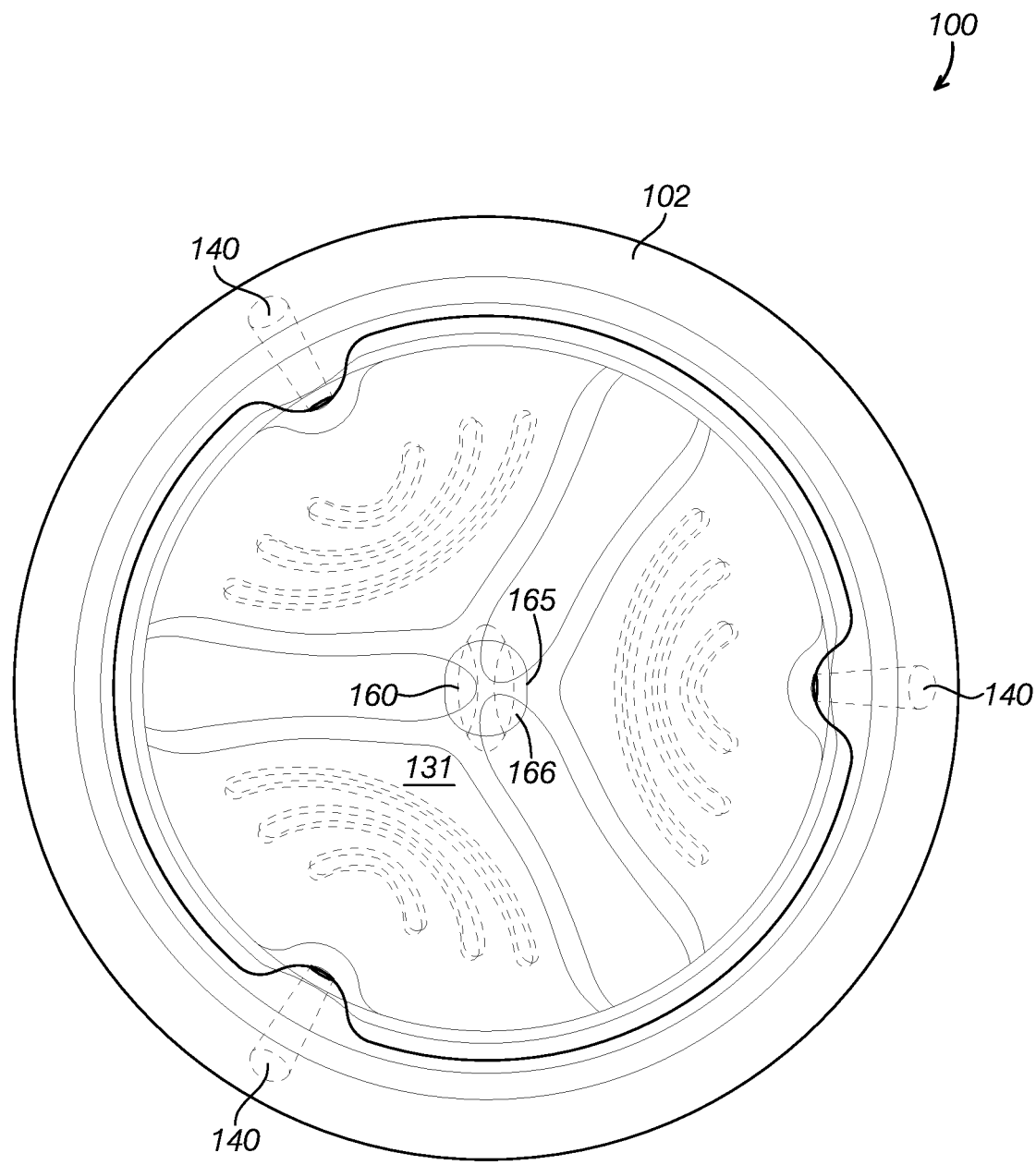
FIG. 5 is a plan view of the menstrual cup shown in FIG. 1 depicting the stem and the stem receptacle.

As shown in FIG. 1, cup 100 includes a top 101, a lip 102, a bottom 103, an outer wall having an outer wall base (110, 111, respectively), and an inner wall having an inner wall base (130, 131, respectively, with inner wall 130 being shown in more detail in FIG. 3 and inner wall base 131 being shown in more detail in FIG. 5). Cup 100 further comprises a plurality of ridges 132, a plurality of ribs 150, a plurality of apertures 140, and in some embodiments, a stem 160. Cup 100 also comprises a receptacle 165 located at the center of the outer wall base 111 comprising a base of stem 160 and a repository 166, whereby "repository" is defined as comprising negative space surrounding the base of stem 160 with an opening parallel to the lip 102 of cup 100 (shown in better detail and described in FIGS. 4 and 5). In some embodiments, lip 102 further comprises lip extension 104 (shown in FIG. 3), which comprises a slightly thinner structural width than lip 102 itself. The reader will appreciate that lip 102 comprises a portion of smooth, rounded protruding silicone that is thicker than outer wall and inner wall (110 and 130, respectively) to ensure that cup 100 will open after being folded and inserted and will retain insertion position. In this manner, cup 100 provides increased comfort by preventing rubbing near the opening of the vaginal cavity.

In the example shown in FIG. 1, outer wall base 111 is located on outer wall 110 on the cup bottom 103 and is a substantially rounded hourglass configuration. It should be understood that, in alternative embodiments, the configuration of cup 100, outer wall 110, and outer wall base 111 may comprise a cylindrical, conical, or other suitable shape sufficient to accomplish cup 100's purposes. In still further embodiments, the shape of outer body 100 may be custom-fitted to each individual user's unique biological measurements. In this manner, it is an object of the present invention to accommodate users of varying body types. Further, the reader will appreciate that outer wall 110 and inner wall 130 are substantially congruous whereby inner wall 130 is adjacent to the inside of cup 100. Thus, outer wall 110 and inner wall 130 form the body of the cup and work in concert such that inner wall 130 forms the inside of cup 100 and comprises a fillable void that is designed to collect catamenia during menses while outer wall 110 forms the outside of the cup in contact with the vaginal wall.

The reader will also appreciate that the components of cup 100 may comprise thin pliant material to aid in flexibility and movability of the cup within the vaginal cavity. In a preferred embodiment, cup 100 is made of a non-toxic, hypoallergenic, elastomeric material such as medical grade silicone. In this manner, cup 100 provides increased flexibility and movability that permits it to conform to the unique shape of each individual user without the need for customization. However, as mentioned above, the dimensions of cup 100 make it capable of being customized should the user's biology and/or body type require it. It should also be understood that it is an object of the present invention that the components of cup 100 are designed to conforms to the natural shape of an individual woman without caving or folding and retains enough structural integrity to remain open to prevent leakage, but pliant enough to conform and move with the user's body. Thus, the reader will appreciate that the components of cup 100 (described in the following figures) work in concert to prevent catamenia from leaking from the vagina during menses. Thus, cup 100 presents a substantial improvement over existing menstrual cups because it is pliant enough to be opened, firm enough to remain opened and prevent leakage, but soft enough to conform and move with the body of the user. Finally, in some embodiments, there may be a gradient decrease in thickness of material of the cup towards the horizontal center, while the lip and base portions remain thicker.

Figure 2:
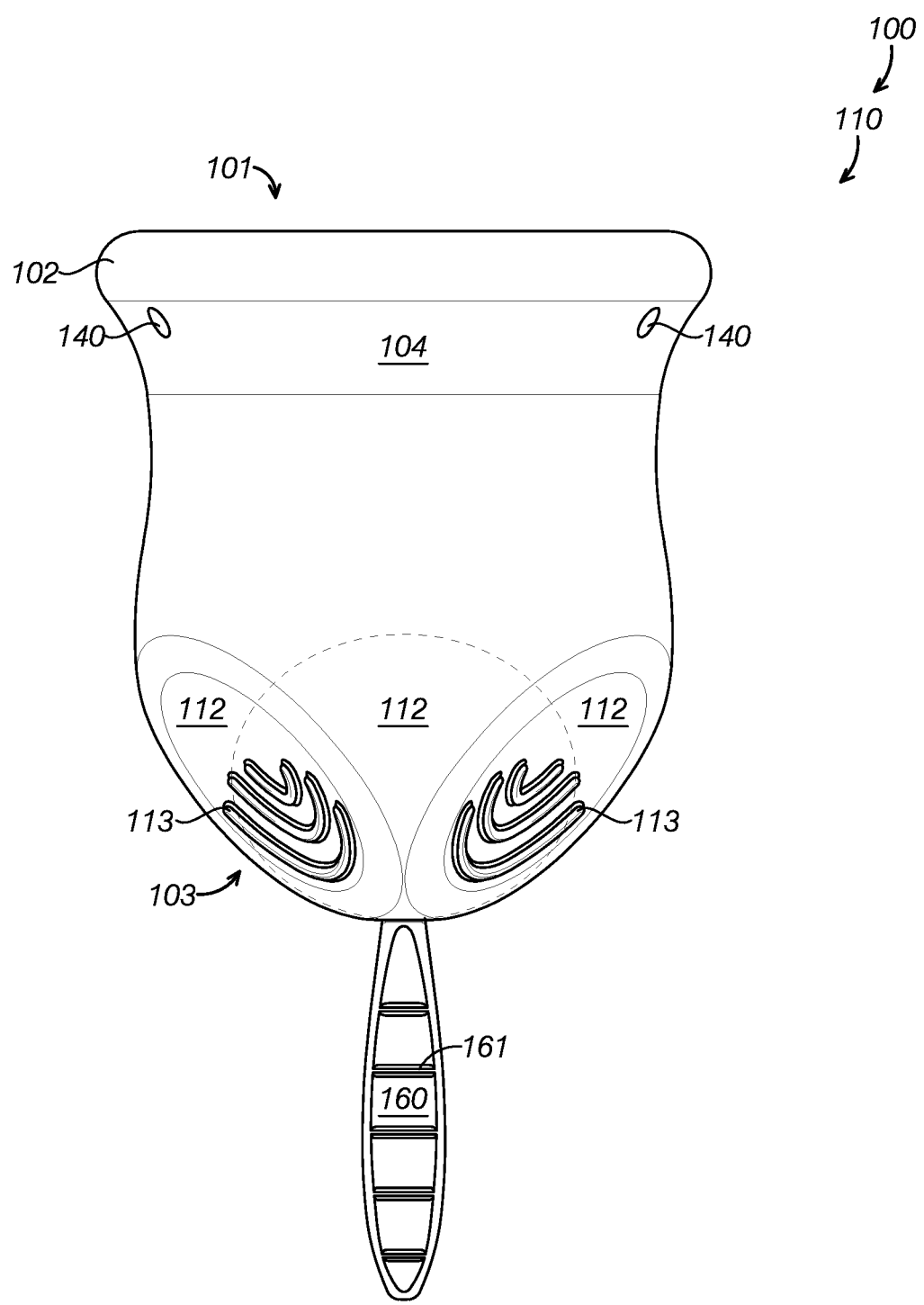
FIG. 2 is an alternative view of the menstrual cup shown in FIG. 1 depicting the outer wall of the cup.

Referring now to FIG. 2, an alternative view of the cup 100 is shown depicting outer wall 110. As can be seen in FIG. 2, and as mentioned above, the components of the outside of cup 100 include outer wall 110, outer wall base 111, lip 102, the plurality of apertures 140 and stem 160. It should be understood that, in alternative embodiments (not shown), stem 160 is an optional feature and its presence or absence does not affect the overall effectiveness of cup. Finally, the outside of cup 100 further comprises a plurality on indentations 112 having indicia 113 and lip extension 104.

With respect to the plurality of apertures 140, FIG. 2 depicts two of the plurality of apertures 140, however it is an object of the present invention that more or less aperture 140 may be employed. In a preferred embodiment of cup 100, the plurality of apertures 140 comprises three apertures 140. As can be seen in the embodiment according to FIG. 2, each of said plurality of apertures 140 is positioned around the perimeter of top 101 and slightly below lip 102 on lip extension 104. Each of the said plurality of apertures 140 comprises a channel traversing outer wall 110 and inner wall 130 on the horizontal plane (shown in FIGS. 1 and 3). In a preferred embodiment, each aperture may be formed at an angle through the thickest part of outer wall 110 and inner wall 130 beneath lip 102. In this manner, each aperture 140, in combination with outer wall 110, inner wall 130, and rib 150 functions to provide improved suction and suction-release upon insertion and removal of cup 100 (discussed in further detail below).

FIG. 2 also illustrates a plurality of indentations 112. As can be seen, indentation 112 may be positioned to substantially circle outer wall base 111 as shown. By way of example, FIG. 2 shows the number of indentations to be three, which is the preferred embodiment, however it is an object of the present invention that more or less indentation 112 may be utilized according to the user's body type and needs. However, it should be understood that the number of indentations is at least two in any embodiment of cup 100.

The reader will appreciate that it is an object of the present invention for each indentation to provide a suitable means for the user to grasp cup 100 for insertion and removal. Further, by way of example, FIG. 2 depicts indentation 112 to be substantially ovoid in shape, however it is an object of the present invention that indentation 112 may be of any shape (such as circular, rectangular, triangular etc.) sufficient to permit the user to properly grasp and collapse cup 100 in situ for effective suction break of aperture 140 and removal of cup 100. Thus, when the user wishes to remove cup 100, she will gently pinch a first indentation 112 against a second indentation 112, thus decreasing the inner volume of cup 100. In this manner, air enters aperture 140, suction is broken, and the cup may be removed. Thus, cup 100 functions to create a superior seal with the walls of the vagina when cup 100 is in use.

In a preferred embodiment, indentation 112 comprises a thickened area of elastomeric material on inner wall base 131 and comprises slightly thicker elastomeric material on outer wall base 111. As can be seen, each of the plurality of indentations 112 circles bottom 103. Further, indentation 112 may comprise a thickened area of elastomeric material that continues from bottom 103 upward to the approximate vertical center of the cup body to allow full expansion when in use.

Further, indentation 112 may comprise a plurality of indicia 113. In the embodiment according to FIG. 2, indicia 113 comprises three, semicircular raised portions that will make pinching, gripping and removing the cup more ergonomic for the fingers. In this manner, indentation 112 provides an ergonomic fit to facilitate insertion and removal of cup 100. The reader will appreciate that the current form of indicia 113 is by way of example only. In alternative embodiments (not shown), at least one of the plurality of indentations 112 may further comprise indicia 113 such as whorls, patterns, or other indicia that provide a graspable portion of indentation 112. The reader will also appreciate that the preferred embodiment of cup 100 does not require indicia 113 to be uniform with respect to each indentation 112. It is an object of the present invention that indicia 113 may comprise indentations, raised portions, or other suitable patterns that may or may not change from indentation to indentation. In this manner, cup 100 allows the user to more easily pinch bottom 103 to break suction for removal of cup 100. In a preferred embodiment, bottom 103, outer wall base 110, and indentation 112 are rounded and smooth for comfort, but are structured such that indentation 112 is set off from outer wall base 111 such that a grip can be made with the users fingers.

Finally, in some embodiments, (not shown) outer wall 110 may further comprise textures, indentations, or other indicia that facilitate gripping and removal of cup 100 and prevent slipping. In still further embodiments, outer wall 110 and inner wall 130 may comprise a matte finish that is moderately transparent to enable the user to determine the amount of catamenia collected. In still further embodiments, outer wall 110 and inner wall 130 may comprise a thinner structural width than the remaining components of cup 100. In this manner outer wall 110 and inner wall 130 increase cup 100's flexibility and movability within the vaginal cavity. Thus, the user is better equipped to break the suction seal of cup 100 in situ and accomplish facilitated removal.

With reference to FIGS. 3 and 4, perspective (FIG. 3) and bisected (FIG. 4) views of cup 100 are shown, depicting inner wall 130. In a preferred embodiment, inner wall 130 and outer wall 110 comprise a thicker structural width than the remaining components of cup 100. As can be seen in FIG. 4, and as mentioned above, outer wall 110 and inner wall 130 are congruous such that the former comprises the outside of the cup and the latter comprises the inside of the cup.

As shown in FIGS. 3 and 4, cup 100 further comprises a plurality of ridges 132 and a plurality of ribs 150 (also shown in FIG. 1). As can be seen, the plurality of ribs 150 and the plurality of ridges 132 may be positioned around the perimeter of inner wall 130. In the present embodiment, each of the plurality of ridges 132 is located on inner wall 130 between indentations 112 as shown. Further, each ridge 132 extends from inner wall base 131 to approximately the vertical center of cup 100. In alternative embodiments (not shown), more or less of each of said plurality of ridges 132 may extend from inner wall base 131 to approximately the vertical center of cup 100, in still further embodiments (not shown), one or more of the plurality of ridges 132 may extend from inner wall base 131 to lip 102. The reader will appreciate that the plurality of ridges 132 functions to facilitate expansion of cup 100 and provide improved gripping means when the plurality of indentations 112 is depressed for cup 100 insertion.

By way of example, the figures depict the number of ridges 132 to be three, however more or less ridges 132 may be included within the present invention according to the user's needs. It should be understood that it is an object of the present invention that the number of ridges may vary according to the user's needs. In alternative embodiments (not shown) ridge 132 may be omitted from the device. In still alternative embodiments (not shown) a second plurality of ridges 132 may be positioned around the perimeter of outer body 110.

FIGS. 3 and 4 also depict a plurality of ribs 150. As can be seen, each of the plurality of ribs 150 is located on inner wall 130, positioned to intersect each of the said plurality of indentations 112 terminating at lip 102. By way of example, FIG. 3 shows the number of ridges 132 and ribs 150 to be 3, however it is an object of the present invention that more or less ribs and ridges may be utilized according to the user's body type and needs. In a preferred embodiment, rib 150 comprises a raised portion a long raised piece thickened material traversing inner wall 130. By way of example, FIG. 3 shows the number of ridges 132 and ribs 150 to be 3, however it is an object of the present invention that more or less ribs and ridges may be utilized according to the user's body type and needs. In a preferred embodiment, rib 150 comprises a raised portion a long raised piece thickened material traversing inner wall 130.

According to the embodiment in the present figures, each of plurality of ribs 150 may substantially circle inner wall 130 and may be substantially adjacent to each of the plurality of ridges 132 as shown. In a preferred embodiment, the number of ribs 150 is equal to the number of apertures 140 and ridges 132 and may be substantially perpendicular to and extend downward away from aperture 140. In this manner, rib 150 works in tandem with aperture 140 to redirect ventilation from the aperture 140 to a substantially lower point on cup 100, thereby facilitating release of suction and removal of cup 100 within the user's body. The finger indentations on the outer base in concert with the vertical ribs aid in the suction release when the cup is pinched at the base by releasing suction at the apertures at the top of the cup. In this manner, the overall volume of cup 100 is not as compromised when suction is released. The user will appreciate that the gentle suction that keeps cup 100 in place in situ is improved and release of the same is improved.

Finally, cup 100 may further comprise stem 160. As can be seen, a base of the stem 160 is located within receptacle 165 substantially in the center of outer wall base 111 surrounded by the negative space of repository 166. In the present embodiment, stem 160 may comprise a flattened tab, however it is an object of the present invention that stem 160 and in other embodiments it may comprise a ring, a nub, or other configuration sufficient to facilitate grasping of outer wall base 111.

The reader will appreciate that stem 160 may used to locate the cup in situ and may be used in conjunction with outer wall base 111 to assist the user with breaking suction and removing the cup. Thus, stem 160 provides an additional means for cup 100 to be easy to reach and remove. Further, it should be understood that stem 160 comprises pliant material that is soft and flexible such that bruising, chafing, rubbing, or other irritation of the vaginal cavity is minimized. In some embodiments, stem 160 may further compromise indicia 161 that provide instructions to trim the stem for customization to the individual user's body or to provide increased gripping capabilities for removal of cup 100. In the present embodiment, stem indicia 161 comprise a plurality of slightly raised and rounded lip in increments on the stem to aid in grip-ability of the stem. In alternative embodiments (not shown) indicia 161 may comprise notches, nubs, markings, or any other indicia suitable for its intended purpose.

Referring now to FIG. 5, a plan view of cup 100 is shown depicting receptacle 165 and stem 160 is shown. As can be seen, receptacle 165 is located in the bottom center of cup 100 and comprises a base of the stem 160 and repository 166. Repository 166 (as shown in FIG. 4) is capable of housing stem 160. In the present embodiment, receptacle 165 functions to permit trimming stem 160 but maintain a smooth base for the comfort of the user. In this manner, if the user wishes to remove stem 160 completely, she may do so by safely trimming it to the inside of receptacle 165 whereby the negative space of the repository 166 encompasses the remaining portion of the stem 160, thus preventing any harmful and/or uncomfortable jagged edges from coming in contact with the vaginal wall or opening.

Based on the preceding description, the reader will appreciate that, when in use, cup 100 is folded or compressed and is inserted into the user's vagina and functions to ensure cup 100 will expand back to the unfolded configuration. When in situ, cup 100 is placed in the vaginal canal such that it is substantially facing the cervix while lip 102 remains in contact with the vaginal walls via gentle suction.

Figure 6:
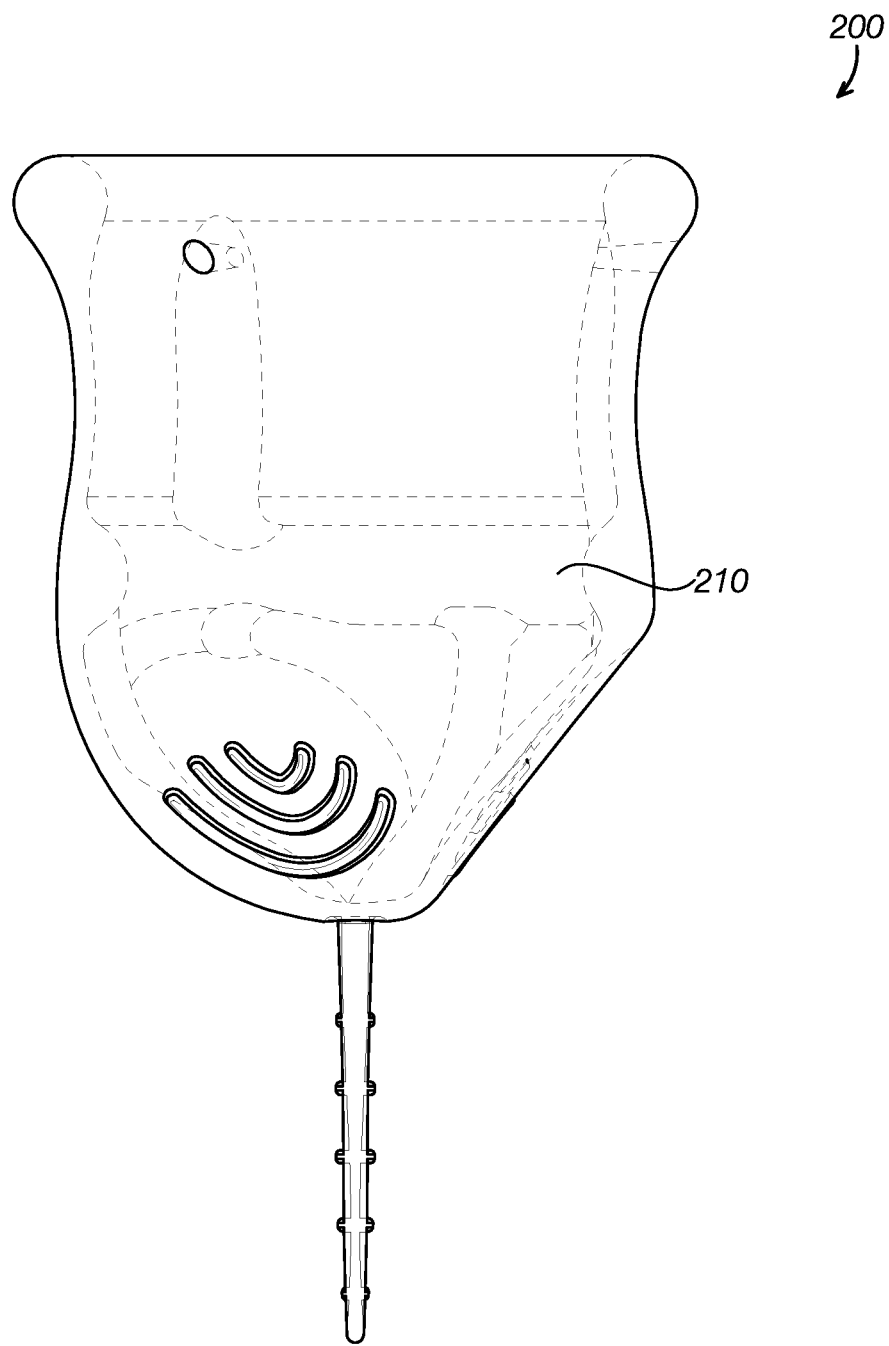
FIG. 6 is a perspective view of a second example of a cup including a circumferential band.
Figure 7:
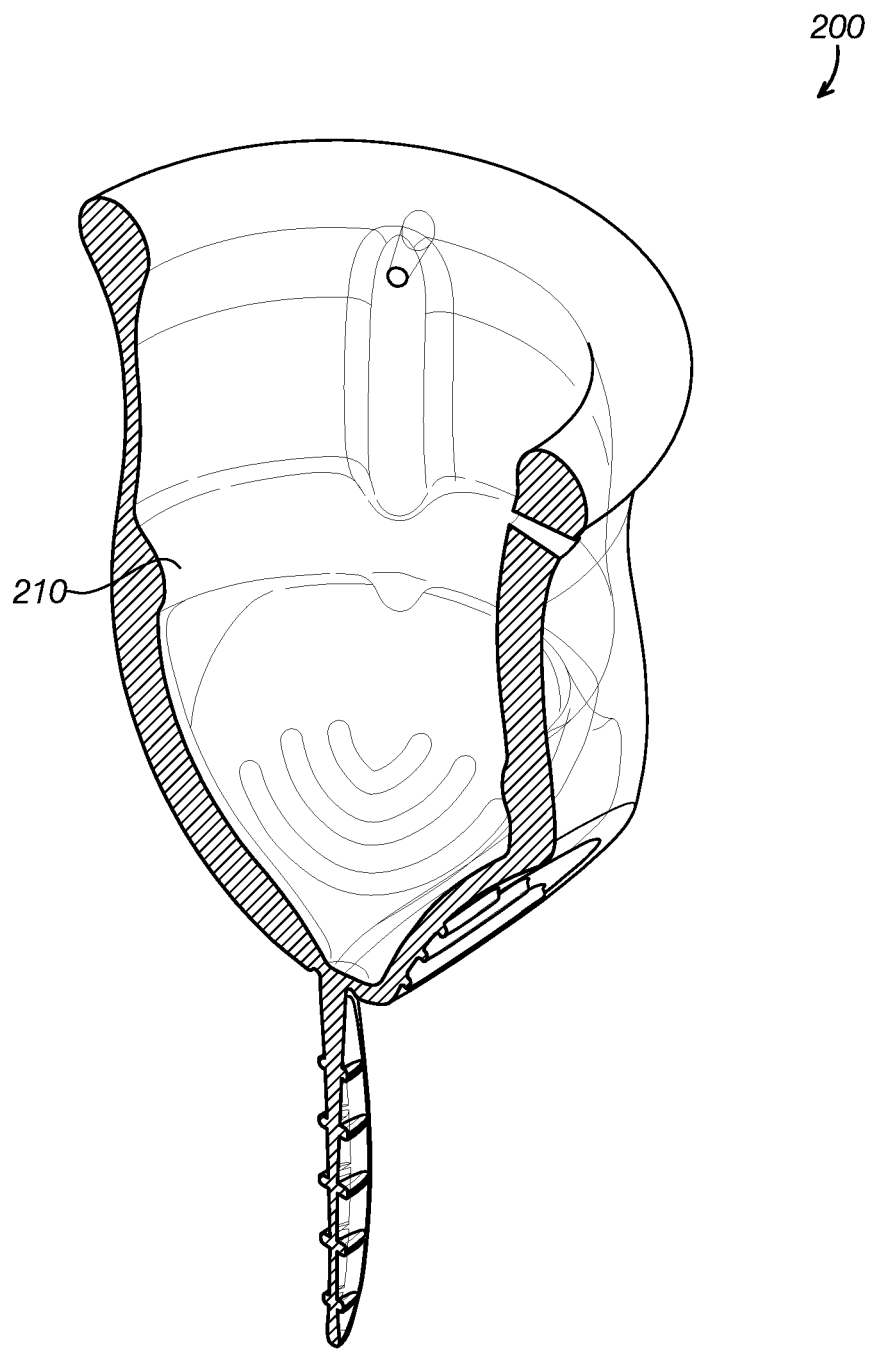
FIG. 7 is a bisected view of the menstrual cup in FIG. 6 depicting the inner wall of the cup.

Turning attention finally to FIGS. 6 and 7, a second example of a reusable cup for collecting catamenia, cup 200 will now be described. Cup 200 includes many similar or identical features to cup 100. Thus, for the sake of brevity, each feature of cup 200 will not be redundantly explained. Rather, key distinctions between cup 200 and cup 100 will be described in detail and the reader should reference the discussion above for features substantially similar between the two cups.

As can be seen in FIG. 6, cup 200 includes band 210. As can be seen, band 210 may be built into the inner wall 130 substantially near the horizontal center of cup 100. In this manner, band 210 facilitates the use of a thinner width of inner wall 130. In this manner, cup 100 may be collapsed for insertion, provides support for inner wall 130 and outer wall 110, and facilitates proper expansion of cup in situ. In a preferred embodiment, band 210 may be implemented in a cross section of inner wall 130 as shown. In alternative embodiments, band 210 may be positioned in other configurations before insertion, such as for example, vertically, accordion style, or any other folding configuration capable of collapsing cup 200 according to the user's body type and specific needs. It should be understood that it is an object of the present invention that band 210 acts as an additional means to help the cup fully expand once in situ. Band 210 also acts as an additional seal for leak protection.

As mentioned above, for the sake of brevity, each feature of cup 200 will not be redundantly explained. Rather, key distinctions between cup 200 and cup 100 will be described in detail and the reader should reference the discussion above for features substantially similar between the two cups. Thus, the reader will appreciate that cup 200 comprises a plurality of ribs 150, ridge 132, and aperture 140. However, in the embodiment according to FIGS. 5 and 6, it can be seen that band 210 bisects cup 200. Thus, the plurality of ridges 132 extends from the base of cup 200 in a similar manner as cup 100, however, each of the plurality of ridges 132 terminates at band 210 as shown. In alternative embodiments (not shown) one or more of the said plurality may terminate near the vertical center of cup 100. In still further embodiments, one or more of said plurality may terminate at lip 102. Similarly, the plurality of ribs 150 begins at the top of indentation 132 (as opposed to the base of cup 100 as discussed in the preceding figures) and terminates at the lip in the manner described above.

The disclosure above encompasses multiple distinct inventions with independent utility. While each of these inventions has been disclosed in a particular form, the specific embodiments disclosed and illustrated above are not to be considered in a limiting sense as numerous variations are possible. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A reusable cup for collecting catamenia, the cup comprising a fillable void, a top, a bottom, a horizontal plane and a vertical plane, and wherein the cup is substantially hollow and further comprises:
    an outer wall having an outer wall base;
    an inner wall that is congruous with the outer wall and comprises an inner wall base wherein the inner wall base is nested within the outer wall base;
    a plurality of apertures; a plurality of ridges, each of said ridges having a top and a bottom;
    a plurality of ribs, each of said ribs having a top and a bottom;
    a stem wherein the stem is attached to the outer wall base;
    a lip whereby the lip is positioned at the top of the cup; and
    a receptacle comprising a repository, wherein the stem is attached to the outer wall base via the receptacle, wherein the stem comprises a pliant material configured to be trimmed, and wherein the receptacle is configured to prevent the stem, in a trimmed configuration, from contacting a user while the cup is in use, whereby the trimmed stem is entirely contained within the receptacle and the repository.

2. The reusable cup of claim 1, wherein the outer wall base is on the bottom of the cup, is substantially rounded and wherein the outer wall base comprises a plurality of outer wall base indentations, each of said plurality of outer wall base indentations having raised indicia.

3. The reusable cup of claim 2, wherein the inner wall further comprises a plurality of inner wall base indentations substantially adjacent to the outer wall base indentations.

4. The reusable cup of claim 3, wherein each of the plurality of ridges is located on the inner wall adjacent to the fillable void, wherein each of the said plurality of ridges begins at the inner wall base and extends on the vertical plane, and wherein each of said plurality of ridges is located substantially between two of the said plurality of inner wall base indentations.

5. The reusable cup of claim 1, wherein the inner wall base is on the bottom of the cup adjacent to the outer wall base, and wherein the inner wall base is substantially rounded.

6. The reusable cup of claim 1, wherein each of the said plurality of apertures comprises a channel traversing the outer wall and the inner wall on the horizontal plane.

7. The reusable cup of claim 1, wherein the receptacle comprising the repository is substantially located centrally in the bottom of the outer wall base and whereby the repository is capable of housing the trimmed stem.

8. The reusable cup of claim 1, wherein the stem further comprises a plurality of indicia.

9. The reusable cup of claim 1, wherein each of the plurality of ribs is located on the inner wall adjacent to the fillable void, wherein each of the plurality of ribs extends from the inner wall base, wherein each of the plurality of ribs extends on the vertical plane, and wherein each of said plurality of ribs is located substantially below each of the plurality of apertures, and wherein the top of each of said plurality of ribs terminates at the lip.

10. A reusable cup for collecting catamenia, the cup comprising a fillable void, a top, bottom, a horizontal plane and a vertical plane, and wherein the cup is substantially hollow and further comprises:

an outer wall having an outer wall base;

an inner wall having an inner wall base, wherein the inner wall base is nested within the outer wall base, and the inner wall further comprises a circumferential band on the horizontal plane, whereby the circumferential band bisects the cup on the horizontal plane substantially between the inner wall base and the top;

a plurality of apertures;

a plurality of ridges, each of said plurality of ridges having a top and a bottom;

a plurality of ribs, each of said plurality of ribs having a top and a bottom;

a stem wherein the stem is attached to the outer wall base;

a lip whereby the lip is positioned at the top of the cup; and a receptacle comprising a repository, wherein the stem is attached to the outer wall base via the receptacle, wherein the stem comprises a pliant material configured to be trimmed, and wherein the receptacle is configured to prevent the stem, in a trimmed configuration, from contacting a user while the cup is in use, whereby the trimmed stem is entirely contained within the receptacle and the repository.

11. The reusable cup of claim 10, wherein the outer wall base is on the bottom of the cup, is substantially rounded and wherein the outer wall base comprises a plurality of outer wall base indentations, each of said plurality of outer wall base indentations having raised indicia.

12. The reusable cup of claim 11, wherein the inner wall further comprises a plurality of inner wall base indentations substantially adjacent to the outer wall base indentations.

13. The reusable cup of claim 12, wherein each of the plurality of ridges is located on the inner wall adjacent to the fillable void, wherein the bottom of each of the plurality of ridges is located at the inner wall base and extends on the vertical plane, wherein the top of each of the plurality of ridges is located underneath the circumferential band and wherein each of the plurality of ridges is located substantially between two of the plurality of inner wall base indentations.

14. The reusable cup of claim 10, wherein the inner wall base is on the bottom of the cup adjacent to the outer wall base, and wherein the inner wall base is substantially rounded.

15. The reusable cup of claim 10, wherein each of the said plurality of apertures comprises a channel traversing the outer wall and the inner wall on the horizontal plane.

16. The reusable cup of claim 10, wherein the receptacle comprising the repository is substantially located centrally in the bottom of the outer wall base and whereby the repository is capable of housing the trimmed stem.

17. The reusable cup of claim 10 wherein the stem further comprises a plurality of indicia.

18. The reusable cup of claim 10, wherein each of the plurality of ribs is located on the inner wall, wherein each of said plurality of ribs is positioned to intersect the circumferential band, wherein each of the plurality of ribs is located substantially below each of the plurality of apertures, and wherein each of said plurality of ribs terminates at the lip.

* * * * *